United States Patent
Gehrke et al.

(10) Patent No.: US 10,994,244 B2
(45) Date of Patent: May 4, 2021

(54) APPARATUS AND METHOD FOR WASTE GAS SCRUBBING

(71) Applicants: thyssenkrupp Industrial Solutions AG, Essen (DE); thyssenkrupp AG, Essen (DE)

(72) Inventors: Helmut Gehrke, Bergkamen (DE); Martina Schmitz, Essen (DE); Stephan Buss, Dortmund (DE)

(73) Assignees: thyssenkrupp Industrial Solutions AG, Essen (DE); thysseukrupp AG, Essen (DE)

( * ) Notice: Subject to any disclaimer, the term of this patent is extended or adjusted under 35 U.S.C. 154(b) by 0 days.

(21) Appl. No.: 16/607,135

(22) PCT Filed: Apr. 18, 2018

(86) PCT No.: PCT/EP2018/059822
§ 371 (c)(1),
(2) Date: Oct. 22, 2019

(87) PCT Pub. No.: WO2018/197279
PCT Pub. Date: Nov. 1, 2018

(65) Prior Publication Data
US 2020/0047118 A1 Feb. 13, 2020

(30) Foreign Application Priority Data
Apr. 25, 2017 (DE) .................. 10 2017 108 843.1

(51) Int. Cl.
*B01D 53/75* (2006.01)
*B01D 53/58* (2006.01)
*B01D 53/78* (2006.01)
*B01D 47/06* (2006.01)
*C07C 273/16* (2006.01)

(52) U.S. Cl.
CPC ............. *B01D 53/75* (2013.01); *B01D 47/06* (2013.01); *B01D 53/58* (2013.01); *B01D 53/78* (2013.01); *C07C 273/16* (2013.01)

(58) Field of Classification Search
CPC .. B01D 2251/502; B01D 47/06; B01D 53/62; B01D 2251/512; B01D 53/75;
(Continued)

(56) References Cited

U.S. PATENT DOCUMENTS 4,919,696 A * 4/1990 Higashi .................. B01D 47/06
55/434.4
5,403,568 A 4/1995 Stowe, Jr.
(Continued)

FOREIGN PATENT DOCUMENTS

AT 506546 A 10/2009
CA 2 696 275 C * 5/2014 ............. B01D 53/68
(Continued)

OTHER PUBLICATIONS

English Translation of International Search Report issued in PCT/EP2018/059822, dated Aug. 23, 2018.
(Continued)

*Primary Examiner* — Timothy C Vanoy
(74) *Attorney, Agent, or Firm* — thyssenkrupp North America, LLC (57) ABSTRACT

A device for waste gas scrubbing in a urea plant may be configured such that a waste gas passes along a transportation direction in the duct. The duct may include a first region for removing urea dust particles from the waste gas and a second region for removing chemical compounds from the waste gas, which can be integrated by an acid-base reaction into an aqueous liquid phase. A cross-sectional area of the duct extending perpendicular to the transportation direction in the second region may be greater than a cross-sectional
(Continued)

area extending perpendicular to the transportation direction in the first region. Further, the device may be configured such that the duct extends horizontally at least in sections and/or the transportation direction of the waste gas through the duct extends horizontally in an installed state.

14 Claims, 5 Drawing Sheets

(58) Field of Classification Search
CPC ............ B01D 2251/506; B01D 53/56; B01D 2251/604; B01D 2251/306; B01D 53/18; B01D 53/504; B01D 2251/404; B01D 53/78; B01D 53/68; B01D 53/58; B01D 2251/504; B01D 2251/304; B01D 2251/2062; C07C 273/16; C07C 273/14
See application file for complete search history.

(56) References Cited

U.S. PATENT DOCUMENTS

| | | | |
|---|---|---|---|
| 6,506,348 B1 | 1/2003 | Ochi | |
| 7,906,089 B2 * | 3/2011 | Ghosh | B01D 53/18 |
| | | | 423/210 |
| 2007/0039469 A1 | 2/2007 | Niehues | |
| 2009/0169450 A1 * | 7/2009 | Naito | B01D 53/75 |
| | | | 423/210 |
| 2011/0280779 A1 | 11/2011 | Gehrke | |
| 2012/0219484 A1 * | 8/2012 | Clark | B01D 53/62 |
| | | | 423/234 |
| 2015/0238897 A1 | 8/2015 | Molgaard | |

FOREIGN PATENT DOCUMENTS

| | | |
|---|---|---|
| DE | 102012111185 A | 5/2014 |
| JP | H 09-085040 A | 3/1997 |
| JP | H 11-137954 A | 5/1999 |
| JP | 2000001466 A | 1/2000 |
| JP | 2002-035545 A | 2/2002 |
| JP | 2004-358294 A | 12/2004 |
| JP | 2007-507333 A | 3/2007 |
| WO | 2015170293 A | 11/2015 |

OTHER PUBLICATIONS

Curbing Nitrogen Plant Emissions, Finishing with Emissions, Fertilizer International 469, (Nov.-Dec. 2015), pp. 25-31.

* cited by examiner

APPARATUS AND METHOD FOR WASTE GAS SCRUBBING

CROSS REFERENCE TO RELATED APPLICATIONS

This application is a U.S. National Stage Entry of International Patent Application Serial Number PCT/EP2018/059822, filed Apr. 18, 2018, which claims priority to German Patent Application No. DE 10 2017 108 843.1, filed Apr. 25, 2017, the entire contents of both of which are incorporated herein by reference.

FIELD

The present disclosure generally relates to waste gas scrubbing, including devices for waste gas scrubbing.

BACKGROUND

Horizontal and vertical devices for waste gas scrubbing are known to a person skilled in the art:

U.S. Pat. No. 5,403,568 discloses a device for the two-step removal of sulfur dioxide from hot flue gases. This is a so-called horizontal washer here, in which the hot flue gas flows through the device in the horizontal direction, wherein a vertically extending spraying device having spray nozzles is provided, which spray an aqueous washing medium, which is sprayed in a flow parallel to the flow of the flue gas. In this horizontal washer, multiple spraying devices spaced apart from one another are provided, which are all used, however, to remove a gas, namely sulfur dioxide, from the gas flow and are thus functionally identical. This horizontal washer moreover has a rectangular housing, the effective cross-sectional area of which is equal in the following washing devices as in the first washing device. A device is also provided downstream to remove liquid from the gas flow. An alkaline washing solution, which contains lime, is used to remove sulfur dioxide in this known device.

*Finishing with Emissions*, Fertilizer International 469, November/December 2015, pages 25-31, discloses a device for the multistep removal of dust particles and ammonia from waste gases.

An apparatus for gas scrubbing is described in DE 10 2012 111 185 A1, in particular for removing carbon dioxide from flue gas by means of amine scrubbing. This known apparatus comprises a cooling stage for the direct cooling and the pre-scrubbing of a gas flow entering the apparatus by means of a liquid supplied to the cooling stage. It is not explicitly stated that this pre-scrubbing is used to remove dust particles from the flue gas. Subsequently, the gas flow reaches an absorption stage, to which a washing liquid is supplied. The washing stage contains column installations to enlarge the exchange area for a material exchange between the gas flow and the washing liquid, wherein the column installations can consist of filler bodies or structured packing materials. The cooling stage can be designed as a spraying apparatus having a plurality of spray nozzles. This known apparatus is a washing tower, in which the cooling stage and the absorption stage are arranged vertically one over another in a single device. The flue gas to be purified by means of the gas scrubbing flows through the washing tower in the vertical direction.

However, the known devices and methods for waste gas scrubbing are not satisfactory in every aspect and a demand exists for improved devices and methods.

Thus a need exists for devices and methods for waste gas scrubbing that improve the efficiency of removing dust particles from waste gas, particularly urea dust particles and certain chemical compounds including ammonia.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present disclosure generally relates to devices for waste gas scrubbing. In one example, a device may comprise a duct having an inlet opening and an outlet opening, wherein the device is de-signed in such a way that a waste gas passes, along a transportation direction (T) in the duct, a first region for removing dust particles from the waste gas, and a second region for removing chemical compounds from the waste gas, which can be integrated into an aqueous phase by an acid-base reaction. A cross-sectional area of the duct extending perpendicularly to the transportation direction (T) in the second region may be greater than a cross-sectional area extending perpendicularly to the transportation direction (T) in the first region. The present disclosure also relates to methods for waste gas scrubbing and urea plants having such devices for waste gas scrubbing.

Devices of the present disclosure may be provided to separate dust particles and chemical compounds, which can be integrated into an aqueous liquid phase by an acid-base reaction, in order to prevent officially predetermined threshold values from being exceeded in the waste gas emitted by the device. For this purpose, the waste gas may be conducted through a device and may pass in succession a first region, in which dust particles are removed from the waste gas, and a second region, in which the mentioned chemical compounds are removed from the waste gas. In this case, the waste gas may be conducted in each case through a liquid shower wherein, in a first step, the dust particles are separated or knocked down by the liquid shower and, in a second step the mentioned chemical compounds react with at least one component of the liquid shower used in this step and thus enter the aqueous liquid phase.

In one example, a device may be integrated into a urea plant. More specifically, an example device of the present disclosure may be provided to have urea dust particles separated or knocked down in a first region and to remove gaseous ammonia by integration into the aqueous liquid phase in a second region, by utilizing an acid that forms ammonium in the washing solution by reaction and then accordingly results in the removal of ammonia.

A first aspect of the invention relates to a device (1) for waste gas scrubbing, wherein the device comprises a duct (5) having an inlet opening (10) and an outlet opening (20), wherein the device (1) is designed in such a way that a waste gas passes, along a transportation direction (T) in the duct (5), a first region (11) for removing dust particles from the waste gas and a second region (12) for removing chemical compounds from the waste gas, which can be integrated by an acid-base reaction into an aqueous liquid phase, wherein a cross-sectional area of the duct (5) extending perpendicularly to the transportation direction (T) in the second region (12) is greater than a cross-sectional area extending perpendicularly to the transportation direction (T) in the first region (11).

"Transportation direction of the waste gas" means the x axis in a three-dimensional coordinate system. "Direction extending perpendicularly to the transportation direction of the waste gas" means the z axis in a three-dimensional coordinate system, which extends toward the center of the earth, the destination of gravity. "Along the transportation direction of the waste gas" means the way of considering it in which the waste gas, after entering the duct (5), first passes the first region (11), which is closest to the inlet opening (10), and last passes the second region (12), which is closest to the outlet opening (20).

In relation to devices known from the prior art, the cross-sectional area in the second region (12) changes in relation to that of the first region (11). The term "cross-sectional area" is to be understood in the meaning of the application as an area provided by the duct (5) for the conveyance of the waste gas perpendicular to the transportation direction of the waste gas. A comparatively high waste gas speed, which is favorable for a separation of the dust particles, in particular the urea dust particles, in the first region (11), may advantageously be reduced in the second region (12) in relation to the first region (11) by the change of the cross-sectional area. A result of the reduced waste gas speed is a lengthened dwell time in the second region (12), which promotes a transition of the mentioned chemical compounds, in particular the ammonia, from the gas phase into the liquid phase and thus the separation of the mentioned chemical compounds, in particular the ammonia. It may thus be taken into consideration in particular by the device according to the invention that different waste gas speeds are advantageous for the various separation processes in the first (11) and second region (12) with regard to the efficiency thereof for the separation.

A cross-sectional area of the duct (5) extending perpendicularly to the transportation direction (T) in the first region (11) preferably corresponds to the cross-sectional area of the inlet opening (10) extending perpendicularly to the transportation direction (T).

A cross-sectional area of the duct (5) extending perpendicularly to the transportation direction (T) in the second region (12) preferably corresponds to the cross-sectional area of the outlet opening (20) extending perpendicularly to the transportation direction (T).

The second region (12) preferably does not comprise a single cross-sectional area of the duct (5) extending perpendicularly to the transportation direction (T) which is less than a cross-sectional area of the duct (5) extending perpendicularly to the transportation direction (T) in the first region (11) and/or which is equal in size to a cross-sectional area of the duct (5) extending perpendicularly to the transportation direction (T) in the first region (11). The maximum cross-sectional area of the duct (5) extending perpendicularly to the transportation direction (T) in the second region (12) is preferably greater than the maximum cross-sectional area of the duct (5) extending perpendicularly to the transportation direction (T) in the first region (11).

The first region (11) preferably does not comprise a single cross-sectional area of the duct (5) extending perpendicularly to the transportation direction (T) which is greater than a cross-sectional area of the duct (5) extending perpendicularly to the transportation direction (T) in the second region (12) and/or which is equal to a cross-sectional area of the duct (5) extending perpendicularly to the transportation direction (T) in the second region (12). The maximum cross-sectional area of the duct (5) extending perpendicularly to the transportation direction (T) in the first region (11) is preferably less than the maximum cross-sectional area of the duct (5) extending perpendicularly to the transportation direction (T) in the second region (12).

The maximum cross-sectional area of the duct (5) in the first region (11) is preferably at least 3 $m^2$, or at least 6 $m^2$, or at least 9 $m^2$, or at least 12 $m^2$, or at least 15 $m^2$, or at least 18 $m^2$, or at least 21 $m^2$, or at least 24 $m^2$, or at least 27 $m^2$, or at least 30 $m^2$, or at least 33 $m^2$, or at least 36 $m^2$, or at least 39 $m^2$, or at least 42 $m^2$, or at least 45 $m^2$. The maximum cross-sectional area of the duct (5) in the first region (11) is preferably less than 45 $m^2$, or 42 $m^2$, or 39 $m^2$, or 36 $m^2$, or 33 $m^2$, or 30 $m^2$, or 27 $m^2$, or 24 $m^2$, or 21 $m^2$, or 18 $m^2$, or 15 $m^2$, or 12 $m^2$, or 9 $m^2$, or 6 $m^2$, or 3 $m^2$.

The maximum cross-sectional area of the duct (5) in the second region (12) is preferably at least 3 $m^2$, or at least 6 $m^2$, or at least 9 $m^2$, or at least 12 $m^2$, or at least 15 $m^2$, or at least 18 $m^2$, or at least 21 $m^2$, or at least 24 $m^2$, or at least 27 $m^2$, or at least 30 $m^2$, or at least 33 $m^2$, or at least 36 $m^2$, or at least 39 $m^2$, or at least 42 $m^2$, or at least 45 $m^2$. The maximum cross-sectional area of the duct (5) in the second region (12) is preferably less than 45 $m^2$, or 42 $m^2$, or 39 $m^2$, or 36 $m^2$, or 33 $m^2$, or 30 $m^2$, or 27 $m^2$, or 24 $m^2$, or 21 $m^2$, or 18 $m^2$, or 15 $m^2$, or 12 $m^2$, or 9 $m^2$, or 6 $m^2$, or 3 $m^2$.

A cross-sectional area of the duct (5) in the second region (12) is preferably greater by at least 5% or at least 10% or at least 15% or at least 20% or at least 25% or at least 30% or at least 35% or at least 40% or at least 45% or at least 50% or at least 55% or at least 60% or at least 65% or at least 70% than the maximum cross-sectional area extending perpendicularly to the transportation direction (T) in the first region (11). If the maximum cross-sectional area extending perpendicularly to the transportation direction (T) in the first region (11) is, for example, 10 m², and if a cross-sectional area of the duct (5) in the second region (12) is greater by at least 10%, a cross-sectional area extending perpendicularly to the transportation direction (T) in the second region (12) is then at least 11 m².

The maximum cross-sectional area of the duct (5) in the first region (11) is preferably less by at least 5% or at least 10% or at least 15% or at least 20% or at least 25% or at least 30% or at least 35% or at least 40% or at least 45% or at least 50% or at least 55% or at least 60% or at least 65% or at least 70% less than a cross-sectional area extending perpendicularly to the transportation direction (T) in the second region (12). If a cross-sectional area extending perpendicularly to the transportation direction (T) in the second region (12) is, for example, 10 m², and if the maximum cross-sectional area of the duct (5) in the first region (11) is less by at least 10%, then the maximum cross-sectional area extending transversely to the transportation direction (T) in the first region (11) is at most 9 m².

The cross-sectional area of the duct (5) in the second region (12) is preferably greater by at least 5% and at most 10%; or at least 10% and at most 20%; or at least 15% and at most 30%; or at least 20% and at most 40%; or at least 25% and at most 50%; or at least 30% and at most 60%; or at least 35% and at most 70%; or at least 40% and at most 80%; or at least 45% and at most 90% than the maximum cross-sectional area extending perpendicularly to the transportation direction (T) in the first region (11). If the maximum cross-sectional area extending perpendicularly to the transportation direction (T) in the first region (11) is, for example, 10 m², and if a cross-sectional area of the duct (5) in the second region (12) is by at least 10% and at most 20% greater, then a cross-sectional area extending perpendicularly to the transportation direction (T) in the second region (12) is at least 11 m² and at most 12 m².

The maximum cross-sectional area of the duct in the first region (11) is preferably at least 5% and at most 10%; or at least 10% and at most 20%; or at least 15% and at most 30%; or at least 20% and at most 40%; or at least 25% and at most 50%; or at least 30% and at most 60%; or at least 35% and at most 70%; or at least 40% and at most 80%; or at least 45% and at most 90% less than a cross-sectional area extending perpendicularly to the transportation direction (T) in the second region (12). If a cross-sectional area extending perpendicularly to the transportation direction (T) in the second region (12) is, for example, 10 m², and if the maximum cross-sectional area of the duct in the first region (11) is at least 10% and at most 20% less, the maximum cross-sectional area extending perpendicularly to the transportation direction (T) in the first region (11) is at least 8 m² and at most 9 m².

A change of the cross-sectional area preferably takes place between the first region (11) and the second region (12) in a direction extending along the transportation direction (T) of the waste gas via a stepped or an inclined profile in one duct wall or multiple duct walls of the duct (5). The change of the cross-sectional area is preferably adapted to the respective situation provided by the installation space of a urea plant.

The length of the duct (5) is preferably at least 2 m, or at least 4 m, or at least 6 m, or at least 8 m, or at least 10 m, or at least 12 m, or at least 14 m, or at least 16 m or at least 18 m or at least 20 m, or at least 22 m, or at least 24 m or at least 26 m or at least 28 m or at least 30 m or at least 32 m. The length of the duct (5) is preferably 2 m to 32 m, or 4 m to 30 m, or 6 m to 28 m, or 8 m to 26 m, or 10 m to 24 m, or 12 m to 22 m, or 14 m to 20 m, or 16 m to 18 m. The length of the duct (5) is preferably less than 32 m, or less than 28 m, or less than 24 m, or less than 20 m, or less than 16 m, or less than 12 m, or less than 8 m, or less than 4 m.

The device is preferably designed in such a way that the duct (5) extends substantially horizontally or substantially vertically in the installed state of the device, in particular integrated in a urea plant. "Horizontal" means (a parallel to the) x axis in a three-dimensional coordinate system. "Vertical" means the z axis in a three-dimensional coordinate system, which extends toward the center of the earth, the destination of gravity.

The length of the first region (11) is preferably at least 2 m, or at least 4 m, or at least 6 m, or at least 8 m, or at least 10 m. The length of the second region (12) is preferably at least 2 m, or at least 4 m, or at least 6 m, or at least 8 m, or at least 10 m. The second region (12) is preferably longer than the first region (11). The first region (11) is preferably longer than the second region (12). The first region (11) and the second region (12) are preferably equal in length.

The waste gas is preferably transported at a speed of greater than 1 m/s, preferably greater than 5 m/s, and particularly preferably greater than 10 m/s through the first region (11). The waste gas is preferably transported at a speed of less than 20 m/s, preferably less than 10 m/s, and particularly preferably less than 5 m/s through the second region (12). The waste gas is preferably transported at a speed of greater than 10 m/s through the first region (11) and of less than 10 m/s through the second region (12), or is transported at a speed of greater than 5 m/s through the first region (11) and of less than 5 m/s through the second region (12), or is transported at a speed of greater than 1 m/s through the first region (11) and of less than 1 m/s through the second region (12). The waste gas speed in the second region (12) is preferably less at every point in time of the waste gas scrubbing than the waste gas speed in the first region (11). The waste gas speed in the first region (11) is preferably greater at every point in time of the waste gas scrubbing than the waste gas speed in the second region (12).

The waste gas entering through the inlet opening (10) preferably has a temperature of at most 140° C., preferably at most 120° C., preferably at most 100° C., preferably at most 80° C., preferably at most 60° C., or preferably at most 50° C.

The dust particles to be removed in the first region (11) preferably have a diameter of greater than 1 μm.

The device (1) according to the invention is preferably integrated into a urea plant, and the waste gas of the urea plant is introduced through the inlet opening (10) into the device (1) and the purified waste gas leaves the device (1) again via the outlet opening (20). In this case, urea dust is separated in the first region (11). This differs from other dusts resulting during industrial operation in particular due to its water solubility. Urea dust is very well soluble in water and also in urea solution. Furthermore, it is possible in the case of urea dust that in the course of the spraying with urea solution and/or water, larger particles of outer layers convert into smaller urea dust particles because of the "washing off". This is not possible with non-water-soluble dust particles. With respect to the geometry of the urea particles, they are substantially round as a result of the genesis thereof. Dust particles from other methods (for example, flue gas desulfurization; $CO_2$ removal from the flue gas of fossil-fuel-fired power plants; or acid processing of fluoride-containing ores) can be shaped differently (polygonal, twinned, agglomerated, etc.). In the second region (12), ammonia is separated in the case of integration in a urea plant.

The following preferred embodiments are to be interpreted in such a way that they apply for the regions (11, 12), for the respective surface enlargement structures (31, 32), for the respective spraying devices (2) contained therein, and for the respective utilized solvents (21, 22) independently of one another, if not explicitly indicated otherwise. For example, "the spraying device (2) for spraying a solvent (21, 22) preferably comprises one or more spray nozzles" is to be understood as a spraying device (2) which is exclusively located in the first region (11) for spraying a first solvent (21); or is to be understood as a spraying device (2), which is exclusively located in the second region (12) for spraying a second solvent (22); or is to be understood as spraying devices (2) which are located in the first region (11) for spraying a first solvent (21) and in the second region (12) for spraying a second solvent (22).

The first region (11) preferably comprises a spraying device (2) for spraying a first solvent (21) and the second region (12) comprises a spraying device (2) for spraying a second solvent (22), i.e., the first region (11) comprises a first surface enlargement structure (31) arranged in the duct (5) for removing dust particles, in particular urea dust particles, and/or the second region (12) comprises a second surface enlargement structure (32) arranged in the duct (5) for removing the mentioned chemical compounds, in particular ammonia. Because the surface enlargement structures (31, 32) are sprayed using the first solvent (21) and/or the second solvent (22), dust particles, in particular urea dust particles, accumulated on the surface enlargement structures (31, 32), are advantageously washed off and/or the mentioned chemical compounds, in particular ammonia, pass from the gas phase to the by the film forming on the surface enlargement structures (31, 32) into the respective washing solution, whereby the washed-off regions of the surface enlargement structures (31, 32) can be provided to the waste gas for renewed accumulation of the dust particles, in particular urea dust particles, and/or the mentioned chemical compounds, in particular ammonia. It is to be noted that ammonia is not separated with identical physical properties as urea dust.

The first region (11) for removing dust particles, in particular urea dust particles, preferably comprises multiple steps and/or the second region (12) for removing the mentioned chemical compounds, in particular ammonia, comprises multiple steps. In this case, the first region (11) and/or the second region (12) comprise(s) multiple surface enlargement structures (31, 32), wherein the first surface enlargement structures (31) in the first region (11) are each sprayed using a first solvent (21) and/or the second surface enlargement structures (32) in the second region (12) are each sprayed using a second solvent (22). By means of the individual steps, the dust particle content, in particular that of urea dust particles, and/or the content of the mentioned chemical compounds, in particular the ammonia content, can be reduced further. In this case, the individual steps are arranged in succession along the transportation direction (T) of the waste gas.

The spraying device (2) for spraying a solvent (21, 22) preferably comprises one or more spray nozzles. The spraying device (2) preferably comprises one or two or three or four or five or six or seven or eight or nine or ten spray nozzles. The spraying device (2) preferably comprises at least one or at least two or at least three or at least four or at least five or at least six or at least seven or at least eight or at least nine or at least ten spray nozzles. The spraying device (2) preferably comprises at least one and at most ten spray nozzles, or at least two and at most nine spray nozzles, or at least three and at most eight spray nozzles, or at least four and at most seven spray nozzles.

The spraying device (2) for spraying a solvent (21, 22) preferably comprises a distributor pipe. A distributor pipe is a device into which multiple spray nozzles are integrated and are supplied with solvent (21, 22) via a common line. A distributor pipe preferably comprises two or three or four or five or six or seven or eight or nine or ten spray nozzles. A distributor pipe preferably comprises at least two or at least three or at least four or at least five or at least six or at least seven or at least eight or at least nine or at least ten spray nozzles. A distributor pipe preferably comprises at least two and at most ten spray nozzles, or at least three and at most nine spray nozzles, or at least four and at most eight spray nozzles, or at least five and at most seven spray nozzles.

The spraying device (2) for spraying a solvent (21, 22) preferably comprises multiple distributor pipes. The spraying device (2) preferably comprises two or three or four or five or six or seven or eight or nine or ten distributor pipes. Preferably, each individual distributor pipe comprises two or three or four or five or six or seven or eight or nine or ten spray nozzles. Each individual distributor pipe preferably comprises at least two or at least three or at least four or at least five or at least six or at least seven or at least eight or at least nine or at least ten spray nozzles. Each individual distributor pipe preferably comprises at least two and at most ten spray nozzles, or at least three and at most nine spray nozzles, or at least four and at most eight spray nozzles, or at least five and at most seven spray nozzles.

The spraying device (2) for spraying a solvent (21, 22) preferably comprises two to ten distributor pipes, which comprise at least twenty spray nozzles. The spraying device (2) preferably comprises two to nine distributor pipes, which comprise at least eighteen spray nozzles. The spraying device (2) preferably comprises two to eight distributor pipes, which comprise at least sixteen spray nozzles. The spraying device (2) preferably comprises two to seven distributor pipes, which comprise at least fourteen spray nozzles. The spraying device (2) preferably comprises two to six distributor pipes, which comprise at least twelve spray nozzles. The spraying device (2) preferably comprises two to five distributor pipes, which comprise at least ten spray nozzles. The spraying device (2) preferably comprises two to four distributor pipes, which comprise at least eight spray nozzles. The spraying device (2) preferably comprises two to three distributor pipes, which comprise at least six spray nozzles.

The spraying device (2) for spraying a solvent (21, 22) preferably comprises one or more distributor pipes, which comprise multiple spray nozzles, and one or more spray nozzles, which are not comprised by distributor pipes. The spraying device (2) preferably comprises at least one distributor pipe, which comprises at least two spray nozzles, and at least one spray nozzle, which is not comprised by distributor pipes. The spraying device (2) preferably comprises at least two distributor pipes, which comprise at least four spray nozzles, and at least two spray nozzles, which are not comprised by distributor pipes. The spraying device (2) preferably comprises at least three distributor pipes, which comprise at least six spray nozzles, and at least three spray nozzles which are not comprised by distributor pipes. The spraying device (2) preferably comprises at least four distributor pipes, which comprise at least eight spray nozzles, and at least four spray nozzles which are not comprised by distributor pipes. The spraying device (2) preferably comprises at least five distributor pipes, which comprise at least ten spray nozzles, and at least five spray nozzles which are not comprised by distributor pipes. The spraying device (2) preferably comprises at least six distributor pipes, which comprise at least twelve spray nozzles, and at least six spray nozzles, which are not comprised by distributor pipes.

The spray nozzles are preferably of the same type. All spray nozzles are preferably either hollow cone nozzles or full cone nozzles or flat jet nozzles or full jet nozzles or spiral nozzles or atomizer nozzles.

At least one spray nozzle is preferably a hollow cone nozzle. At least one spray nozzle is preferably a full cone nozzle. At least one spray nozzle is preferably a flat jet nozzle. At least one spray nozzle is preferably a full jet nozzle. At least one spray nozzle is preferably a spiral nozzle. At least one spray nozzle is preferably an atomizer nozzle.

The spray nozzles are preferably of different types. At most one spray nozzle is preferably a full cone nozzle. At most one spray nozzle is preferably a flat jet nozzle. At most one spray nozzle is preferably a full jet nozzle. At most one spray nozzle is preferably a spiral nozzle. At most one spray nozzle is preferably an atomizer nozzle.

Gaseous ammonia is preferably integrated into the aqueous liquid phase and removed from the device (1). In the liquid phase, the ammonia reacts instantaneously with an acid washing solution and forms ammonium ions. The ammonia partial pressure above the liquid phase is approximately zero due to this ammonium ion formation, so that it is possible to remove the ammonia from the gas phase.

According to the present invention, ammonia is particularly preferably removed from the gas flow in the second region, i.e., acid scrubbing takes place.

Preferably,
gaseous ammonia, and/or
gaseous $NO_x$, and/or
gaseous $NO_2$, and/or
gaseous $SO_2$, in particular in the case of flue gas desulfurization, and/or
gaseous $CO_2$, in particular in the case of $CO_2$ removal from the flue gas of fossil-fuel-fired power plants, and/or
HF, in particular in the case of the acid processing of fluoride-containing ores, for example, phosphate ores,
is integrated into the aqueous liquid phase and removed from the device (1).

Gaseous reactive components, preferably organic reactive components, are preferably integrated into the aqueous liquid phase and removed from the device (1).

The second solvent (22) comprises at least one component which transfers the gaseous chemical compound into the aqueous liquid phase.

The second solvent (22) preferably comprises an acid washing solution. The acid washing solution preferably comprises sulfuric acid, nitric acid, hydrochloric acid, phosphoric acid, or mixtures of sulfuric acid, nitric acid, hydrochloric acid, and/or phosphoric acid, or mixtures of sulfuric acid, nitric acid, hydrochloric acid, phosphoric acid, and/or urea solution. The acid content of one of the above-mentioned acids or the mixtures of at least two of the abovementioned acids is preferably in the range of 0.01-50.00% by weight, or in the range of 0.01-10.00% by weight, or in the range of 0.1-5.00% by weight, in relation to the total weight of the second solvent (22). Acids suitable for the ammonia separation preferably have a pk(S) value less than 7, or less than 5, or less than 2.5.

The second solvent (22) preferably comprises a base. The second solvent (22) preferably comprises a strong and/or a weak base. The second solvent (22) preferably comprises a strong inorganic and/or a weak inorganic and/or a strong organic and/or a weak organic base. The second solvent (22) preferably comprises sodium hydroxide (NaOH), potassium hydroxide (KOH), ammonia solutions, and/or calcium hydroxide ($Ca(OH)_2$).

The second solvent (22) preferably comprises monofunctional, bi-functional, and/or tri-functional amines, preferably MDEA (methyl diethanolamine).

The first solvent (21) preferably comprises water and/or a urea solution. The first solvent (21) preferably exclusively comprises water or exclusively comprises a urea solution.

The first solvent (21) and the second solvent (22) preferably differ in such a way that the first solvent (21) comprises at least one component which the second solvent (22) does not comprise. The first solvent (21) and the second solvent (22) preferably differ in such a way that the second solvent (22) comprises at least one component which the first solvent (21) does not comprise.

The first (21) and/or the second solvent (22) is preferably dispensed from above or diagonally from below onto the surface enlargement structures (31, 32).

A washing solution which drains off of one of the surface enlargement structures (31, 32) is preferably used for a further spraying of the surface enlargement structures (31, 32), i.e., reused as a first (21) and/or second solvent (22) in an advantageous manner. The drained washing solution is collected and supplied to the spraying device (2) again for this purpose. It is also possible that only a part of the collected washing solution is used and recirculated, but augmented with freshwater and/or fresh acid and/or fresh base.

The surface enlargement structure (31, 32) preferably comprises installations, which result in a corresponding enlargement of the surface, but only provide little resistance to the gas because of the pressure loss generated, however. The surface enlargement structure (31, 32) preferably comprises random bulk materials and/or structured packing materials. The surface enlargement structure (31, 32) preferably comprises random bulk material selected from the group consisting of Raschig rings, saddle elements, spirals, and combinations thereof. The surface enlargement structure (31, 32) preferably comprises structured packing materials selected from the group consisting of fabric packing materials, sheet metal packing materials, stretched metal packing materials, plastic packing materials, grid packing materials, and combinations thereof. The surface enlargement structure (31, 32) preferably comprises random bulk materials selected from the group consisting of Raschig rings, saddle elements, spirals, and combinations thereof, and structured packing materials selected from the group consisting of fabric packing materials, sheet metal packing materials, stretched metal packing materials, plastic packing materials, grid packing materials, and combinations thereof. The surface enlargement structure (31, 32) preferably comprises
  random structural elements selected from the group consisting of Raschig rings, Pall rings, saddle elements, spring-typical elements, and combinations thereof; and/or
  structured structural elements selected from the group consisting of plates, corrugated plates, formed plates, and combinations thereof; and/or
  material selected from the group consisting of metal, glass, plastic, carbon fibers, and combinations thereof.

A second aspect of the present invention is a method for waste gas scrubbing, in particular in a urea plant, wherein a waste gas is guided through a duct (5) having a first region (11) for removing dust particles, in particular urea particles, and a second region (12) for removing the mentioned chemical compounds, in particular ammonia, wherein a waste gas speed at which the waste gas is guided in the duct (5) is greater in the first region (11) than in the second region (12).

The method according to the invention has the advantage over the method known from the prior art that due to the reduced waste gas speed in the second region (12), an enhanced efficiency may be achieved in the separation of the mentioned chemical compounds, in particular ammonia. The reduced waste gas speed in the second region (12) is implemented by an enlargement of the cross-sectional area of the duct (5) in the second region (12) in relation to the first region (11).

A third aspect of the present invention is the use of the device according to the invention for waste gas scrubbing.

Further details, features, and advantages of the invention result from the drawings, and also from the following description of preferred embodiments on the basis of the drawings.

Figure 1:
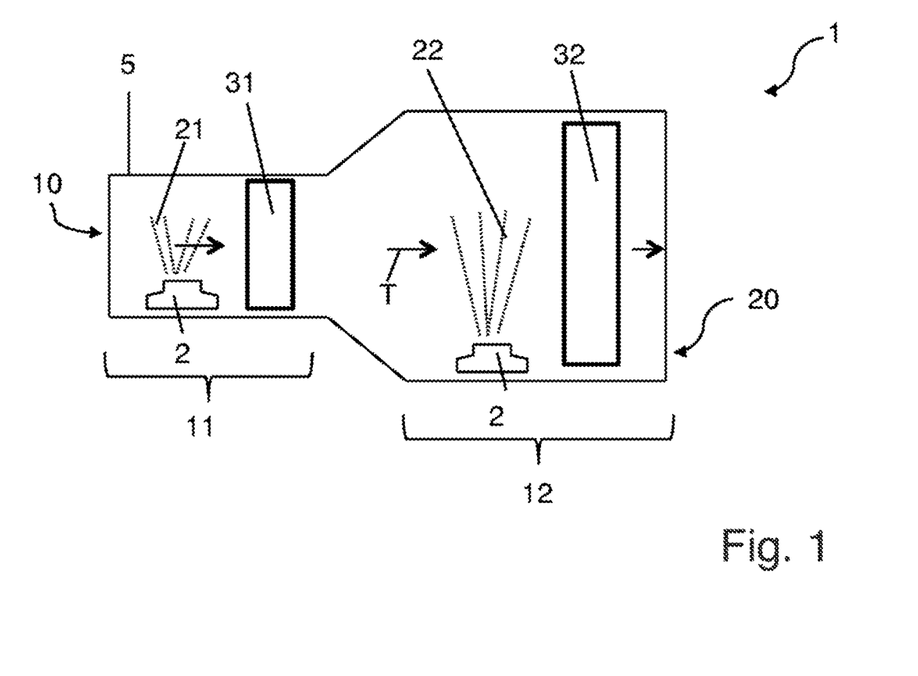
FIG. 1 is a top view of a first example device for waste gas scrubbing.

A device (1) for waste gas scrubbing according to a first exemplary embodiment of the present invention is shown in FIG. 1. In particular, this is a device (1) which is installed in a urea plant and using which the goal is pursued of removing urea dust particles and ammonia from the waste gas sufficiently that the remaining component thereof in the waste gas is below a critical and/or officially prescribed threshold value.

For this purpose, the waste gas is introduced via an inlet opening (10) into a duct (5) of the device (1). On the path to the outlet opening (20) of the device (1), the waste gas passes, along a transportation direction (T) in the duct (5), a first region (11) and a second region (12). It is provided in this case that the waste gas is freed of urea dust particles in the first region (11), while the ammonia is removed from the waste gas in the second region (12). The second region (12) is arranged after the first region (11) along the transportation direction (T).

Furthermore, it is provided for the exemplary embodiment shown in FIG. 1 that the duct (5) extends substantially horizontally in the installed state. Devices of this type are also referred to as horizontal scrubbers.

To remove the urea dust particles, in this case a first surface enlargement structure (31), through which the waste gas is conducted, is sprayed in the first region (11) with the aid of a spraying device (2) using a first solvent (21). The first solvent (21) is preferably water or a urea solution. It is conceivable that the solvent (21) is dispensed from above onto the first surface enlargement structure (31) of the first region (11) and then runs down it driven by gravity (principle of the graduation mechanism). The spraying can also extend in principle from the rear, i.e., in counter flow to the transportation direction (T). The spraying can also extend in principle from the front, i.e., in continuous flow with the transportation direction (T). In principle, the spraying can also take place from the side or from below transversely in relation to the waste gas flow.

The first surface enlargement structure (31), which is finely structured in particular, causes the urea dust particles to be separated on a surface of the first surface enlargement structure (31) by the intrinsic, provided momentum thereof.

The first surface enlargement structure (31) is preferably designed in the first region (11) in such a way that it has the largest possible surface, on the one hand, and only opposes the waste gas with a comparatively low resistance because of the generated pressure loss, on the other hand. For example, random bulk materials or structured packing materials are conceivable.

It is preferably provided that the first surface enlargement structure (31) is sprayed using water or a urea solution by means of further spraying devices (2) (not shown). It is advantageously ensured in this way that in the first region (11), the urea dust particles separated on the surface are washed off from the first surface enlargement structure (31) and thus the surface can be provided for a further separation of further urea dust particles. These "free spaces" of the surface apply in particular to the first region (11).

Since the effectiveness of the dust separation is greater the higher the momentum and thus the speed of the urea dust particles is, comparatively high speeds are advantageous in the first region (11).

To remove ammonia, the second surface enlargement structure (32) is sprayed in the second region (12) with the aid of a spraying device (2), preferably using multiple, in particular equivalent spraying devices (2), using a second solution (22). In the second region (12), fresh washing solution, i.e., having unused acid, is provided again and again to the gas. It is conceivable that the solvent (22) is dispensed from above onto the second surface enlargement structure (32) of the second region (12) and then runs down it driven by gravity (principle of the graduation mechanism). The spraying can in principle also extend from the rear, i.e., in counter flow to the transportation direction (T). The spraying can in principle also extend from the front, i.e., in continuous flow with the transportation direction (T). The second surface enlargement structure (32) in the second region (22) is preferably designed in such a way that it has the largest possible surface area, on the one hand, and only opposes the waste gas with a comparatively low resistance because of the produced pressure loss, on the other hand. Bulk materials or structured packing materials are conceivable, for example.

The second solvent (22) is preferably an acid washing solution, whereby an enhanced material transport of the ammonia out of the gas phase into the liquid phase occurs. For example, the acid washing solution comprises an acid such as sulfuric acid, nitric acid, hydrochloric acid, or phosphoric acid. In the liquid phase, the ammonia reacts instantaneously with the acid washing solution and forms ammonium ions. Due to this ammonium ion formation, the ammonia partial pressure above the liquid phase is approximately zero, so that it is possible to substantially remove the ammonia from the gas phase. The ammonia is preferably removed in the second region (12) in multiple steps, wherein each step comprises at least one surface enlargement structure (32) and at least one spraying device (2). It is provided in particular in this case that a washing solution which is drained off of the second surface enlargement structure (32) is unified and/or collected, and after an elevation of the acid concentration, is sprayed onto the second surface enlargement structure (32) again. The drained washing solution may thus advantageously be reused as the second solvent (22). For example, the spraying device (2) is designed as a single nozzle, as a multilevel nozzle, as a cone pattern nozzle, as a nozzle for providing a square pattern, as a nozzle for providing a jet, or as a nozzle inducing a random solvent distribution.

To improve the removal of the ammonia from the waste gas, it is provided in particular that a waste gas speed at which the waste gas is guided through the duct (5) is reduced in the second region (12) in relation to the waste gas speed in the first region (11). For this purpose, the cross-sectional area of the duct (5) extending perpendicularly to the transportation direction (T) is enlarged in the second region (12) in relation to the cross-sectional area extending perpendicularly to the transportation direction (T) from the first region (11). It is conceivable in this case that the cross-sectional area in the second region (12) is enlarged in the vertical and/or horizontal direction in relation to the cross-sectional area in the first region (11). A dwell time in the second region (12) may thus advantageously be lengthened. Furthermore, the power of a fan at the outlet of the device, i.e., in the region of the outlet opening, could advantageously be reduced by this measure, since at otherwise equal volume flow under normal conditions, the pressure loss via the second surface enlargement structure (32) is reduced and thus the pressure level in the overall device (1) is raised.

Figure 2A:
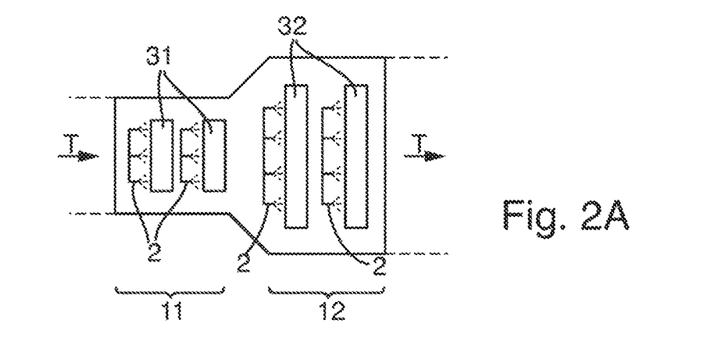
FIG. 2A is a top view of a second example device for waste gas scrubbing.
Figure 2B:
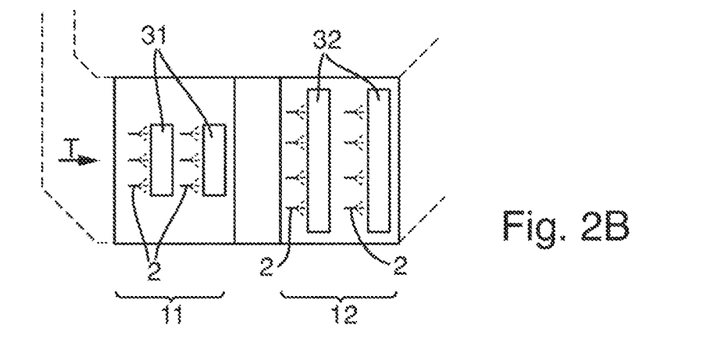
FIG. 2B is a side view of the device of FIG. 2A.

A second alternative exemplary embodiment of the invention is explained hereafter with reference to FIGS. 2A and 2B. Insofar as the plant parts correspond to those according to FIG. 1, the above statements on the exemplary embodiment of FIG. 1 apply, so that they are not repeated here and the corresponding reference signs are also not shown. Therefore, only the differences are explained in greater detail here. In the variant according to FIGS. 2A and 2B, it can be seen in the top view according to FIG. 2A that in the second region (12), the cross section of the duct (5) widens by approximately the same amount toward both sides, so that a horizontal cross-sectional widening symmetrical in relation to the center axis of the duct (5) results. In comparison to FIG. 1, the arrangement of the spraying devices (2) is such that they each spray approximately in the flow direction of the waste gas into the surface enlargement structures (31, 32). FIGS. 2A and 2B show that in each case multiple spraying devices (2) can be arranged both adjacent to one another and also one over another each with spacing in relation to one another for each of the surface enlargement structures (31, 32). These spraying devices (2) are each arranged in front of the surface enlargement structures (31, 32) viewed in the flow direction of the waste gas flow and spray into these structures. FIG. 2B shows that a cross-sectional widening of the duct (5) in the horizontal direction is provided here, but the height of the duct (5), i.e., its vertical extension, is uniform over the length of the duct (5).

Figure 3A:
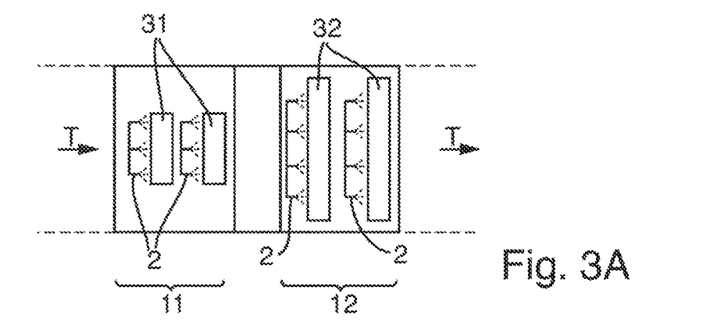
FIG. 3A is a top view of a third example device for waste gas scrubbing.
Figure 3B:
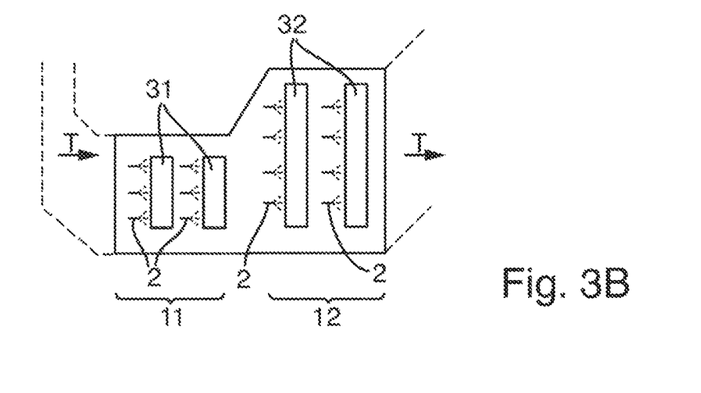
FIG. 3B is a side view of the device according to FIG. 3A.

A third alternative exemplary embodiment of the invention is explained hereafter with reference to FIGS. 3A and 3B. Insofar as the plant parts correspond to those according to FIG. 1, the above statements on the exemplary embodiment of FIG. 1 apply, so that they are not repeated here and the corresponding reference signs are also not shown.

Therefore, only the differences are explained in greater detail here. In the variant according to FIGS. 3A and 3B, it can be seen in the top view according to FIG. 3A that in the second region (12), the cross section of the duct (5) is unchanged in the lateral extension in comparison to the first region (11), but as FIG. 3B shows, the height of the duct (5) is greater in the second region, so that an asymmetrical vertical cross-sectional expansion results. In comparison to FIG. 1, the arrangement of the spraying devices (2) is such that they each spray into the surface enlargement structures (31, 32) approximately in the flow direction of the waste gas. FIGS. 2A and 2B show that in each case multiple spraying devices (2) can be arranged both adjacent to one another and also one over another each with spacing in relation to one another for each of the surface enlargement structures (31, 32). These spraying devices (2) are each arranged in front of the surface enlargement structures (31, 32) viewed in the flow direction of the waste gas flow and spray into these structures. FIG. 3A shows that, for example, only a cross-sectional expansion of the duct (5) in the vertical direction upward is provided here.

Figure 4A:
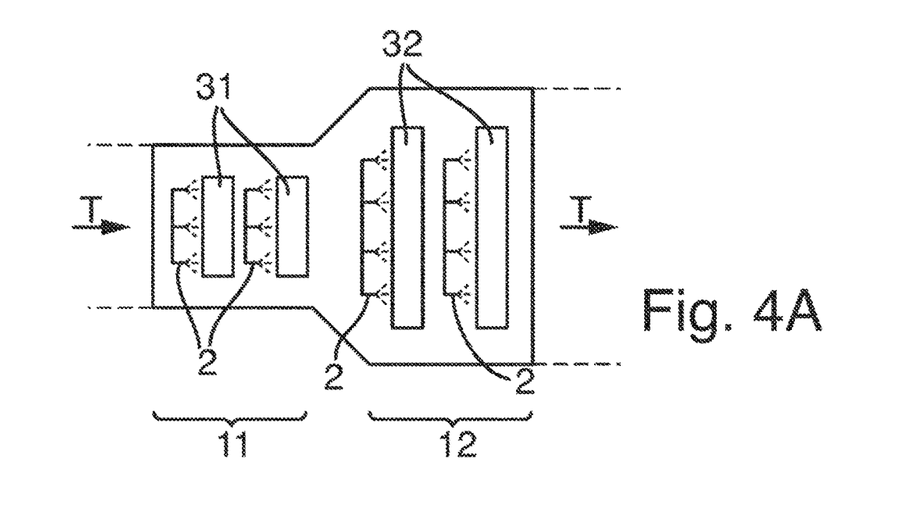
FIG. 4A is a top view of a fourth example device for waste gas scrubbing.
Figure 4B:
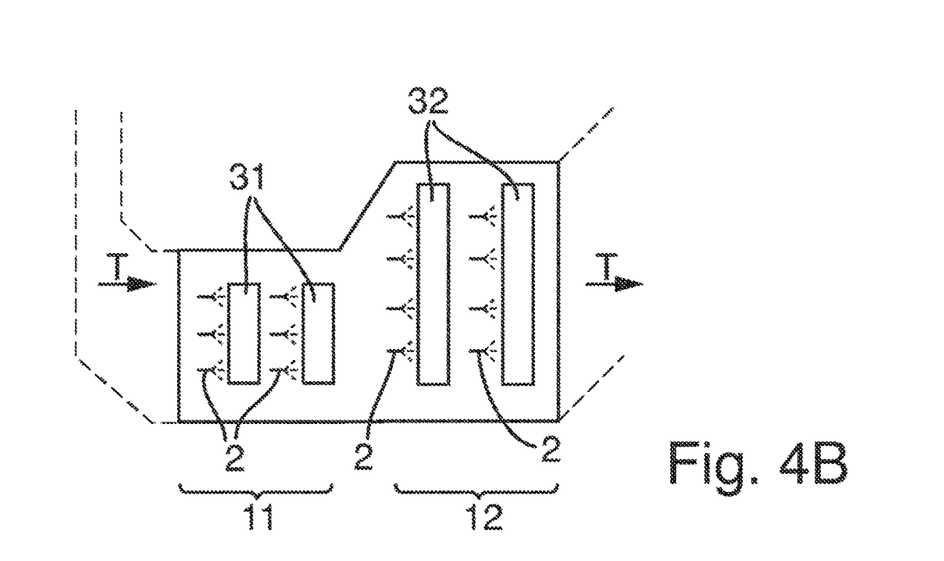
FIG. 4B is a side view of the device according to FIG. 4A.

A fourth alternative exemplary embodiment of the invention is explained hereafter with reference to FIGS. 4A and 4B. Insofar as the plant parts correspond to those according to FIG. 1, the above statements on the exemplary embodiment of FIG. 1 apply, so that they are not repeated here and the corresponding reference signs are also not shown. Therefore, only the differences are explained in greater detail here. In the variant according to FIGS. 4A and 4B, it can be seen in the top view according to FIG. 4A that in the second region (12), the cross section of the duct (5) is symmetrically widened in the horizontal direction toward both sides in the lateral extension in comparison to the first region (11) and additionally, as also shown in FIG. 4B, the height of the duct (5) is greater in the second region (12), so that an asymmetrical vertical cross-sectional expansion additionally results. In comparison to FIG. 1, the arrangement of the spraying devices (2) is such that they each spray into the surface enlargement structures (31, 32) approximately in the flow direction of the waste gas. FIGS. 4A and 4B show that in each case multiple spraying devices (2) can be arranged both adjacent to one another and also one over another each with spacing in relation to one another for each of the surface enlargement structures (31, 32). These spraying devices (2) are each arranged in front of the surface enlargement structures (31, 32) viewed in the flow direction of the waste gas flow and spray into these structures. FIG. 4B shows that in addition to the horizontal cross-sectional expansion, for example, a cross-sectional expansion of the duct (5) in the vertical direction upward is also provided here.

Figure 5A:
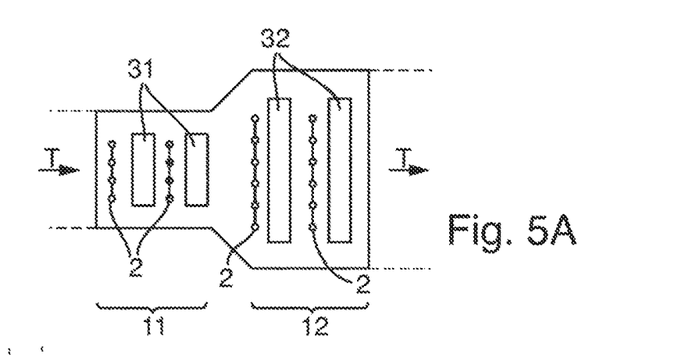
FIG. 5A is a top view of a fifth example device for waste gas scrubbing.
Figure 5B:
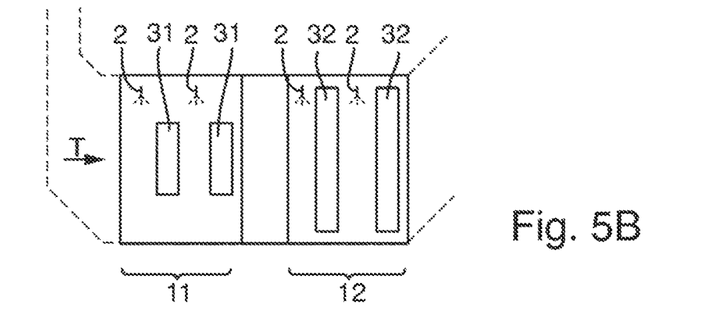
FIG. 5B is a side view of the device according to FIG. 5A.

A fifth alternative exemplary embodiment of the invention is explained hereafter with reference to FIGS. 5A and 5B. Insofar as the plant parts correspond to those according to FIG. 1, the above statements on the exemplary embodiment of FIG. 1 apply, so that they are not repeated here and the corresponding reference signs are also not shown. Therefore, only the differences are explained in greater detail here. In the variant according to FIGS. 5A and 5B, it can be seen in the top view according to FIG. 5A that in the second region (12), the cross section of the duct (5) is widened by approximately the same amount toward both sides, so that a horizontal cross-sectional expansion symmetrical in relation to the center axis of the duct (5) results. In comparison to FIG. 2, however, the arrangement of the spraying devices (2) is here such that they each spray in approximately from above approximately at a right angle (i.e., transversely) to the flow direction of the waste gas into the waste gas flow and do so upstream before the surface enlargement structures (31, 32), so that the spray medium is entrained by the waste gas flow. FIGS. 5A and 5B show that multiple spraying devices (2) arranged adjacent to one another each with spacing in relation to one another can be arranged for each of the surface enlargement structures (31, 32). These spraying devices (2) are each arranged in front of the surface enlargement structures (31, 32) viewed in the flow direction of the waste gas flow and spray in front of these structures and downward. FIG. 5B shows that a cross-sectional expansion of the duct (5) in the horizontal direction is provided here, but the height of the duct (5), i.e., its vertical extension, is uniform over the length of the duct (5).

Figure 6A:
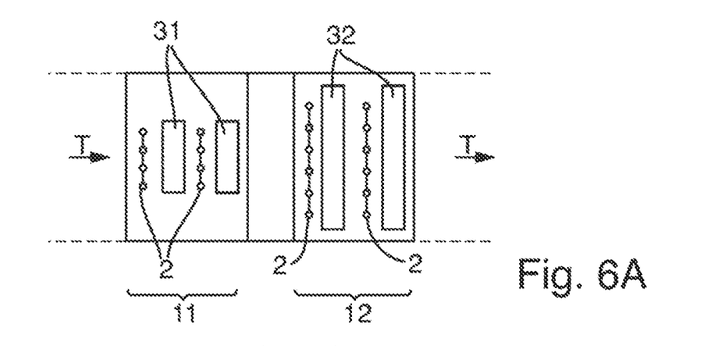
FIG. 6A is a top view of a sixth example device for waste gas scrubbing.
Figure 6B:
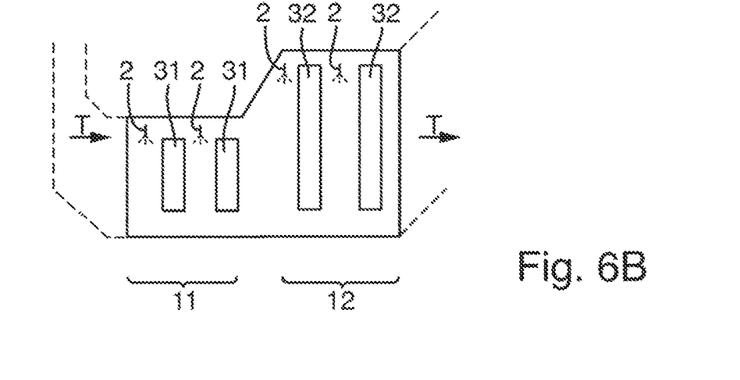
FIG. 6B is a side view of the device according to FIG. 6A.

A sixth alternative exemplary embodiment of the invention is explained hereafter with reference to FIGS. 6A and 6B. Insofar as the plant parts correspond to those according to FIG. 1, the above statements on the exemplary embodiment of FIG. 1 apply, so that they are not repeated here and the corresponding reference signs are also not shown. Therefore, only the differences are explained in greater detail here. In the variant according to FIGS. 6A and 6B, it can be seen in the top view according to FIG. 6A that in the second region (12), the cross section of the duct (5) is unchanged in the lateral extension in comparison to the first region (11), however, as shown in FIG. 6B, the height of the duct (5) is greater in the second region, so that an asymmetrical vertical cross-sectional expansion results. In comparison to FIG. 1, the arrangement of the spraying devices (2) is such that they each spray into the waste gas flow transversely to the flow direction of the waste gas in front of the surface enlargement structures (31, 32). FIGS. 6A and 6B show that in each case multiple spraying devices (2) can be arranged each adjacent to one another and each with spacing in relation to one another for each of the surface enlargement structures (31, 32). These spraying devices (2) are each arranged in front of the surface enlargement structures (31, 32) viewed in the flow direction of the waste gas flow and spray in front of the surface enlargement structures (31, 32) from the upper region of the duct. FIG. 6A shows that only a cross-sectional expansion of the duct (5) in the vertical direction upward is provided here, for example.

Figure 7A:
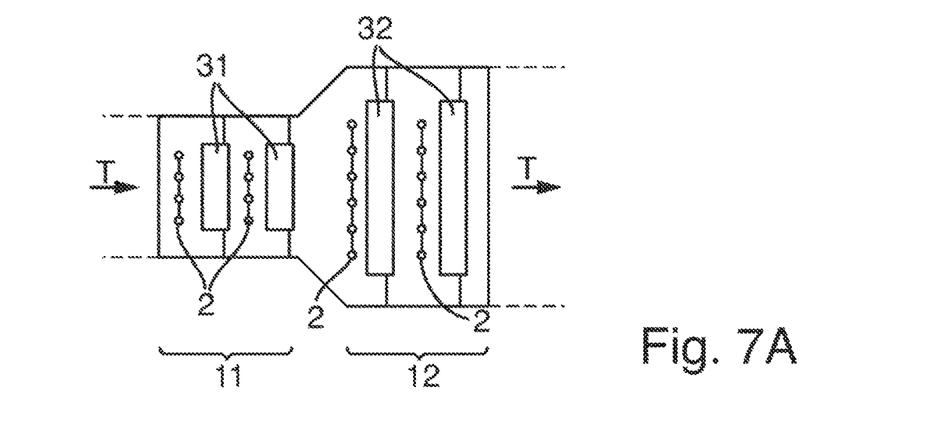
FIG. 7A is a top view of a seventh example device for waste gas scrubbing.
Figure 7B:
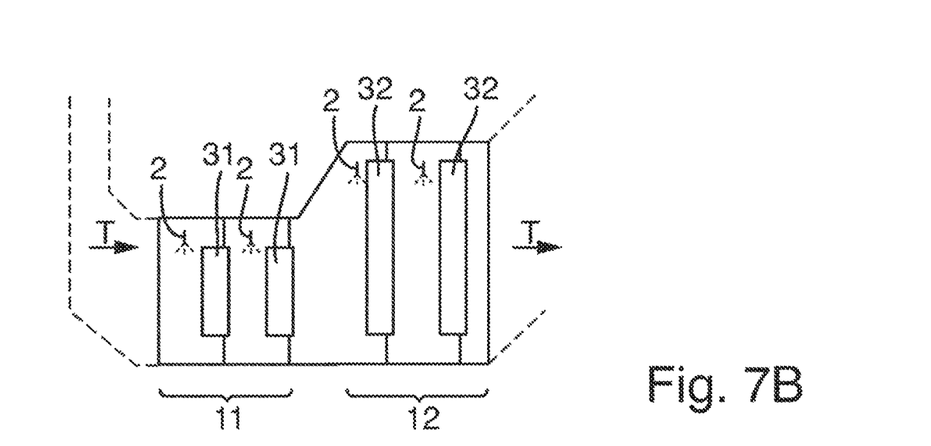
FIG. 7B is a side view of the device according to FIG. 7A.

A seventh alternative exemplary embodiment of the invention is explained hereafter with reference to FIGS. 7A and 7B. Insofar as the plant parts correspond to those according to FIG. 1, the above statements on the exemplary embodiment of FIG. 1 apply, so that they are not repeated here and the corresponding reference signs are also not shown. Therefore, only the differences are explained in greater detail here. In the variant according to FIGS. 7A and 7B, it can be seen in the top view according to FIG. 7A that in the second region (12), the cross section of the duct (5) is symmetrically widened toward both sides in the horizontal direction in the lateral extension in comparison to the first region (11) and additionally, as shown in FIG. 7B, the height of the duct (5) is also greater in the second region (12), so that an asymmetrical vertical cross-sectional expansion additionally results. In comparison to FIG. 1, the arrangement of the spraying devices (2) is such that they each spray in front of the surface enlargement structures (31, 32) and into the waste gas flow from above transversely to the flow direction of the waste gas. FIGS. 7A and 7B show that in each case multiple spraying devices (2) can be arranged each adjacent to one another each in rows with spacing for each of the surface enlargement structures (31, 32), wherein the spraying devices (2) can be arranged farther upward in the second region (12) expanded in cross section as a result of the greater height of the duct (5) than the spraying devices (2) in the first region (11). These spraying devices (2) are each arranged in front of the surface enlargement structures (31, 32) viewed in the flow direction of the waste gas flow and spray into the waste gas flow up-stream in front of these structures from above. FIG. 7B shows that in addition to the horizontal cross-sectional expansion, a cross-sectional expansion of the duct (5) in the vertical direction upward is also for example provided here.

EXPERIMENTAL DATA

The following experiment was carried out to prove the dependence of the efficiency for the ammonia removal from the waste gas on the speed of the gas:

Air enriched with ammonia was introduced into a duct having spraying devices (2) and a second surface enlargement structure (32) as are provided for the second region (12) of the duct from the preceding exemplary embodiment. In this case, the speed of the waste gas inside the duct (5) was regulated and/or set by means of a fan. For the quantitative determination of the efficiency, the ammonia content was measured before entry into the duct (5) and upon exit from the duct (5) and the ammonia reduction was determined according to $1-(NH3,_{out}/NH3,_{in})$. To determine the respective ammonia concentrations, a corresponding partial gas quantity was withdrawn from the gas to be studied and conducted through a precisely known quantity of sulfuric acid. The partial gas quantity is accurately determined by suitable units (gas counters). Ammonium sulfate results due to the reaction of the ammonia with the sulfuric acid, which reduces the proportion of free sulfuric acid. After ending the conduction through, the remaining quantity of still existing sulfuric acid is ascertained by back-titration using lye (sodium hydroxide solution) in a manner familiar to a person skilled in the art. The ammonia concentration in the gas flow can be computed using the data thus obtained.

The result of the measurement was an increase of the reduction of the ammonia content by 2.7% points (which corresponds to an increase of the efficiency by 3.1%) when the gas speed in the duct (5) was reduced by 10%.

LIST OF REFERENCE SIGNS 1 device
2 spraying device
5 duct
10 inlet opening
11 first region
12 second region
20 outlet opening
21 first solvent
22 second solvent
31 surface enlargement structure
32 surface enlargement structure
T transportation direction (T)

What is claimed is:

1. A device for waste gas scrubbing in a urea plant, the device comprising:
 a duct with an inlet opening and an outlet opening, wherein the device is configured such that a waste gas passes along a transportation direction in the duct, wherein the duct extends horizontally at least in sections and/or the transportation direction of the waste gas through the duct extends horizontally in an installed state of the device, wherein the duct comprises:
  a first region comprising a first surface enlargement structure disposed in the duct for removing urea dust particles from the waste gas, and
  a second region comprising a second surface enlargement structure disposed in the duct for removing chemical compounds from the waste gas, which are configured to be integrated by an acid-base reaction into an aqueous liquid phase,
 wherein a cross-sectional area of the duct extending perpendicular to the transportation direction in the second region is greater than a cross-sectional area of the duct extending perpendicular to the transportation direction in the first region,
 wherein the first region comprises a first spraying device for spraying a first solvent, wherein the second region comprises a second spraying device for spraying a second solvent.

2. The device of claim 1 wherein the cross-sectional area in the second region has at least one of a greater height or a greater width than the cross-sectional area of the first region.

3. The device of claim 1 wherein at least one of the first spraying device or the second spraying device comprises a distributor pipe.

4. The device of claim 3 wherein the distributor pipe comprises spray nozzles that are configured to be supplied with one of the solvents via a common feed line.

5. The device of claim 1 wherein at least one of the first spraying device or the second spraying device is disposed so as to spray into a flow of the waste gas from above transversely to the transportation direction of the flow of the waste gas upstream in front of the respective first or second surface enlargement structure.

6. The device of claim 1 wherein at least one of the first spraying device or the second spraying device is disposed upstream in front of the respective first or second surface enlargement structure such that the at least one of the first spraying device or the second spraying device sprays into the respective first or second surface enlargement structure in the transportation direction of a flow of the waste gas.

7. The device of claim 1 wherein at least one of the first surface enlargement structure or the second surface enlargement structure comprises as least one of:
  Raschig rings, Pall rings, saddle elements, spring-typical bodies, or combinations thereof;
  plates, corrugated plates, formed plates, or combinations thereof; or
  metal, glass, plastic, carbon fibers, or combinations thereof.

8. A device for waste gas scrubbing in a urea plant, the device comprising:
  a duct with an inlet opening and an outlet opening, wherein the device is configured such that a waste gas passes along a transportation direction in the duct, wherein the duct extends horizontally at least in sections and/or the transportation direction of the waste gas through the duct extends horizontally in an installed state of the device, wherein the duct comprises:
    a first region comprising a first surface enlargement structure disposed in the duct for removing urea dust particles from the waste gas, and
    a second region comprising a second surface enlargement structure disposed in the duct for removing chemical compounds from the waste gas, which are configured to be integrated by an acid-base reaction into an aqueous liquid phase,
  wherein a cross-sectional area of the duct extending perpendicular to the transportation direction in the second region is greater than a cross-sectional area of the duct extending perpendicular to the transportation direction in the first region,
  wherein at least one of:
    the first region is configured to remove urea dust particles in multiple steps; or
    the second region is configured to remove the chemical compounds in multiple steps, wherein one of the chemical compounds is ammonia.

9. A method for waste gas scrubbing in a urea plant, the method comprising:
  guiding a waste gas through a duct having a first region for removing urea dust particles and a second region for removing chemical compounds from the waste gas, which are configured to be integrated by an acid-base reaction into an aqueous liquid phase; and
  transporting the waste gas through the second region at a lesser speed than in the first region due to an enlargement of a cross-sectional area of the duct that extends perpendicular to a transportation direction in the second region,
  wherein the duct extends horizontally at least in sections and/or the transportation direction of the waste gas through the duct extends horizontally.

10. The method of claim 9 comprising removing ammonia, which is one of the chemical compounds, by way of an acid washing solution in the second region.

11. The method of claim 10 wherein the acid washing solution includes an acid.

12. The method of claim 10 wherein the acid washing solution includes at least one of sulfuric acid, nitric acid, hydrochloric acid, or phosphoric acid.

13. The method of claim 9 comprising:
  transporting the waste gas at a speed of greater than 1 m/s through the first region; and
  transporting the waste gas at a speed of less than 1 m/s through the second region.

14. The method of claim 13 wherein the waste gas entering through an inlet opening of the duct has a temperature of at most 140° C.

* * * * *